(12) United States Patent
Mao et al.

(10) Patent No.: US 8,977,332 B1
(45) Date of Patent: *Mar. 10, 2015

(54) RETRACTOR DEVICE WITH OXIMETER SENSOR AND FORCE SENSOR

(71) Applicants: ViOptix, Inc., Fremont, CA (US); The Regents of the University of California, Oakland, CA (US)

(72) Inventors: Jimmy Jian-min Mao, Fremont, CA (US); Robert E. Lash, Redwood City, CA (US); Shane Burch, San Anselmo, CA (US)

(73) Assignees: ViOptix, Inc., Fremont, CA (US); Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/231,236

(22) Filed: Mar. 31, 2014

Related U.S. Application Data

(63) Continuation of application No. 12/689,053, filed on Jan. 18, 2010, now Pat. No. 8,688,186.

(60) Provisional application No. 61/149,916, filed on Feb. 4, 2009.

(51) Int. Cl.
*A61B 5/00* (2006.01)
*A61B 1/32* (2006.01)
*A61B 17/02* (2006.01)
*A61B 5/1455* (2006.01)

(52) U.S. Cl.
CPC ............ *A61B 17/02* (2013.01); *A61B 5/14551* (2013.01)
USPC ............................ 600/323; 600/202; 600/210

(58) Field of Classification Search
USPC ................. 600/323, 325, 332, 202, 201, 210
See application file for complete search history.

(56) References Cited

U.S. PATENT DOCUMENTS

| | | |
|---|---|---|
| 4,784,150 A | 11/1988 | Voorhies et al. |
| 4,945,896 A | 8/1990 | Gade |
| 5,088,493 A | 2/1992 | Giannini et al. |
| 5,201,325 A | 4/1993 | McEwen et al. |
| 5,584,296 A | 12/1996 | Cui et al. |
| 5,667,517 A | 9/1997 | Hooven |
| 5,687,719 A | 11/1997 | Sato et al. |
| 5,769,781 A | 6/1998 | Chappuis |
| 5,807,377 A | 9/1998 | Madhani et al. |
| 5,879,294 A | 3/1999 | Anderson et al. |
| 6,078,833 A | 6/2000 | Hueber |
| 6,285,904 B1 | 9/2001 | Weber et al. |

(Continued)

OTHER PUBLICATIONS

D. Hueber et al., "New Optical Probe Designs for Absolute (Self-Calibrating) NIR Tissue Hemoglobin Measurements," Proceedings of Optical Tomography and Spectroscopy of Tissue III, Jan. 1999, 618-631, vol. 3597.

(Continued)

*Primary Examiner* — Rochelle-Ann J Blackman
(74) *Attorney, Agent, or Firm* — Aka Chan LLP

(57) ABSTRACT

A retractor device has an oximeter sensor at its tip, which allows measuring of oxygen saturation of a tissue being retracted by the retractor. The retractor device also has a force sensor which can measure an amount of force that is applied to the retracted tissue by the tip of the retractor device. The tip includes one or more openings for at least one source and detector. A specific implementation is a spinal nerve root retractor with an oximeter sensor and a force sensor.

21 Claims, 11 Drawing Sheets

(56) References Cited

U.S. PATENT DOCUMENTS

| | | |
|---|---|---|
| 6,452,354 B1 | 9/2002 | Ellsworth et al. |
| 6,487,343 B1 | 11/2002 | Lewandowski et al. |
| 6,516,209 B2 | 2/2003 | Cheng et al. |
| 6,549,284 B1 | 4/2003 | Boas et al. |
| 6,587,703 B2 | 7/2003 | Cheng et al. |
| 6,597,931 B1 | 7/2003 | Cheng et al. |
| 6,708,048 B1 | 3/2004 | Chance |
| 6,735,458 B2 | 5/2004 | Cheng et al. |
| 6,892,006 B2 | 5/2005 | Lewandowski et al. |
| 7,014,617 B2 | 3/2006 | Grinberg |
| 7,185,590 B2 | 3/2007 | Fu et al. |
| 7,226,413 B2 | 6/2007 | McKinley |
| 7,254,427 B2 | 8/2007 | Cho et al. |
| 7,355,688 B2 | 4/2008 | Lash et al. |
| 7,435,219 B2 | 10/2008 | Kim |
| 8,688,186 B1 * | 4/2014 | Mao et al. .................. 600/323 |
| 2004/0111016 A1 | 6/2004 | Casscells et al. |
| 2008/0319290 A1 | 12/2008 | Mao et al. |
| 2009/0284378 A1 | 11/2009 | Ferren et al. |

OTHER PUBLICATIONS

A. Balakrishnan et al., "Smart Retractor for Use in Image Guided Neurosurgery", 2003 Summer Bioengineering Conference, Jun. 25-29, 2003, Sonesta Beach Resort in Key Biscayne, Florida, pp. 895-896.

U.S. Appl. No. 12/365,735, filed Feb. 4, 2009, Office Action, mailed May 13, 2011 (rejecting claim 6 on p. 12, para. 18, of the office action).

U.S. Appl. No. 12/365,735, filed Feb. 4, 2009, Final Office Action mailed Jan. 26, 2012 (rejecting claim 6 on pp. 7-8, para. 6, and on p. 13, first paragraph).

* cited by examiner 255 force sensor
265 a second handle
241 linear clamp element
243 L-shaped clamp element
215 fastner for clamp
275 cable for force sensor
276 cable for oximeter sensor 216 shaft
213 first handle for retractor
222 tip of retractor
228 retractor blade
231 oximeter sensor
230 sensor opening

RETRACTOR DEVICE WITH OXIMETER SENSOR AND FORCE SENSOR

CROSS-REFERENCE TO RELATED APPLICATIONS

This patent application is a continuation of U.S. patent application Ser. No. 12/689,053, filed Jan. 18, 2010, issued as U.S. Pat. No. 8,688,186 on Apr. 1, 2014, which claims the benefit of U.S. provisional patent application 61/149,916, filed Feb. 4, 2009, which are incorporated by reference.

BACKGROUND OF THE INVENTION

This invention relates to the field of medical devices and more specifically to a retractor device with an oximeter sensor and force sensor.

Retractors play an important role in medicine. Retractors typically retract or hold aside tissue so that a physician (e.g., surgeon) can gain access to an area for operation or observation. It is important to not damage the tissue when retracting the tissue.

One area of medicine that retractors are commonly used is during spinal surgery. Tens of thousands of spinal surgeries are performed each year. The number of spinal surgeries is continuing to increase due, in part, to an aging population, active lifestyles, and a better understanding of what causes back pain. Back pain may be due to disc herniation, degenerative disc disease, spinal trauma, and osteoarthritis just to name a few examples.

The spinal cord is the main pathway through which the brain sends and receives signals. The nerve fibers in the spinal cord branch off to form pairs of nerve roots that travel through small openings between the vertebrae. These nerves control the body's function including the vital organs, sensation, and movement.

During spinal surgery, it is often necessary to retract, or hold, the nerve root aside so that the surgeon can access the surgical site. With current medical devices, however, it is difficult if not impossible, to tell whether the nerve root is being damaged during the retraction. Damage to the nerve root or any nerve is undesirable—leading to loss of sensation, numbness, or pain to patient.

There is, then, a continuing demand for medical devices that provide patient feedback, provide more features, are easier to use, and generally address the needs of patients, doctors, and others in the medical community.

Therefore, there is a need to provide improved devices and techniques for retractors.

BRIEF SUMMARY OF THE INVENTION

A retractor device has a retractor including a shaft, a handle connected to a proximal end of the shaft, and a tip connected to a distal end of the shaft, where the tip has a retractor portion and an oximeter sensor. The retractor device further includes a force sensor that is operatively connected to the retractor.

The oximeter sensor in the device measures oxygen saturation of a tissue being retracted by the retractor device. The force sensor measures an amount of force applied to a retracted tissue by the tip of the retractor device. Thus, the retractor device can simultaneously measure two parameters of a retracted tissue—oxygen saturation level of the retracted tissue contacting the tip of the retractor device and an amount of force applied to the retracted tissue by the tip.

In one implementation, the retractor device is a nerve root retractor device for retracting a nerve. The tissue oxygen saturation sensing capability can potentially prevent nerve root hypoxia during spinal surgical retraction. In addition, force sensor measurements allow a surgeon to monitor and adjust an amount of force applied to a retracted tissue during surgery. Thus, the use of an excessive amount of force, which can potentially damage a tissue, can be avoided during retraction. By having both oximeter sensor and force sensor, the retractor device can better assist determining the effect of surgical manipulation on the health of nerve roots and other tissues.

In another implementation, the retractor device has a force sensor that is an integral part of a retractor, and the force sensor can be located at any suitable location between a handle and a tip of the retractor. For instance, the force sensor has a first end and a second end, the first end and the second end being on opposite side of each other along the axis of the force sensor. The first end of the force sensor can be attached to the handle of the retractor, and the second end of the force sensor can be attached to a proximal end of a shaft of the retractor.

In yet another embodiment, the retractor device can have a force sensor as a separate attachment to the retractor. For instance, the first end of the force sensor is attached to the handle of the retractor by a clamp. The second end of the force sensor is attached to a separate handgrip element or second handle. A surgeon can hold the handgrip element or second handle (not the handle on the retractor itself) to retract a tissue, and an amount of force that is applied to the tissue by the tip of the retractor device is measured by the force sensor.

In yet another implementation, the retractor device has an oximeter sensor including a first sensor opening and a second sensor opening on a bottom side of the tip. There is a first optical fiber and a second optical fiber. The first optical fiber passes through a channel in the shaft and a distal end of the first optical fiber is connected to the first sensor opening of the tip. The second optical fiber passes through the channel in the shaft and a distal end of the second optical fiber is connected to the second sensor opening of the tip.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
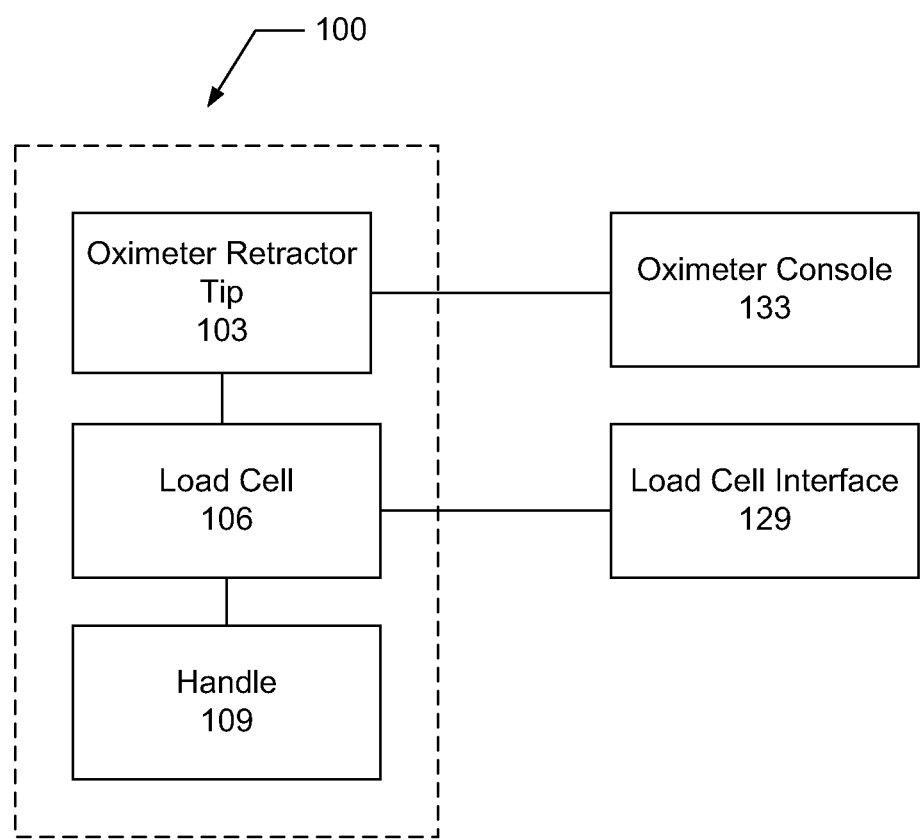
FIG. 1 shows a block diagram of a retractor device with an oximeter sensor and a load cell, and other components.

FIG. 1 shows a block diagram of a retractor device 100 that is used for retracting a tissue, such as a nerve root. Retractor device 100 can also be used to measure oxygen saturation of the retracted tissue and an amount of force applied to the tissue during retraction. FIG. 1 also shows an oximeter console 133 and a load cell interface 129 which are connected to components of retractor device 100.

Retractor device 100 has an oximeter retractor tip 103 which is connected to a force sensor or load cell 106, which is in turn connected to a handle 109. Oximeter retractor tip 103 includes a retractor portion which is used to retract a tissue and an oximeter sensor which is used to measure oxygen saturation level of the tissue contacting the tip. The retractor device is used by placing the oximeter sensor at the retractor tip in contact with a tissue such as a nerve, and the tissue is pulled aside by the retractor tip.

Load cell 106 in the retractor device measures an amount of force that is applied to the tissue by oximeter retractor tip 103 when a surgeon holds handle 109 and retracts or pulls aside the tissue. Load cell 106 is a transducer that converts a force or load acting on it into an electrical signal. When there are changes in the force or load, there will be a change in the electrical signal produced by the load cell. The load cell can be located at any suitable location between oximeter retractor tip 103 and handle 109.

Oximeter console 133 is connected to an oximeter sensor located at oximeter retractor tip 103 by a cable. Light is transmitted from oximeter console 133, through optical fiber in the cable, out a sensor opening on the tip and into the nerve. The reflected light from the nerve is then received by another sensor opening at the tip, transmitted back to the oximeter console via optical fiber. The oximeter console processes and analyzes light information or signals using algorithms and converts the signals into oxygen saturation values in terms of percentage. The oximeter console can include a screen to display the oxygen saturation measurement and the timing of measurement. The measurements can also be stored in the oximeter console.

Load cell interface 129 is connected to load cell 106 of the retractor device by a cable. The signal from load cell 106 is transmitted to load cell interface 129 directly or via circuitry. The load cell interface transforms the electrical signals from the load cell into a force or other measurement or reading, which can be shown on a display.

While oximeter console 133 and load cell console 129 are shown as separate blocks in FIG. 1, these components can be enclosed in a single housing (e.g., a console or computer), or in separate housings. For example, the load cell interface may be incorporated within oximeter console 133. Alternatively, some subcomponents of oximeter console 133 and load cell interface 129 can be combined into a single housing while other subcomponents are housed separately.

Figure 2:
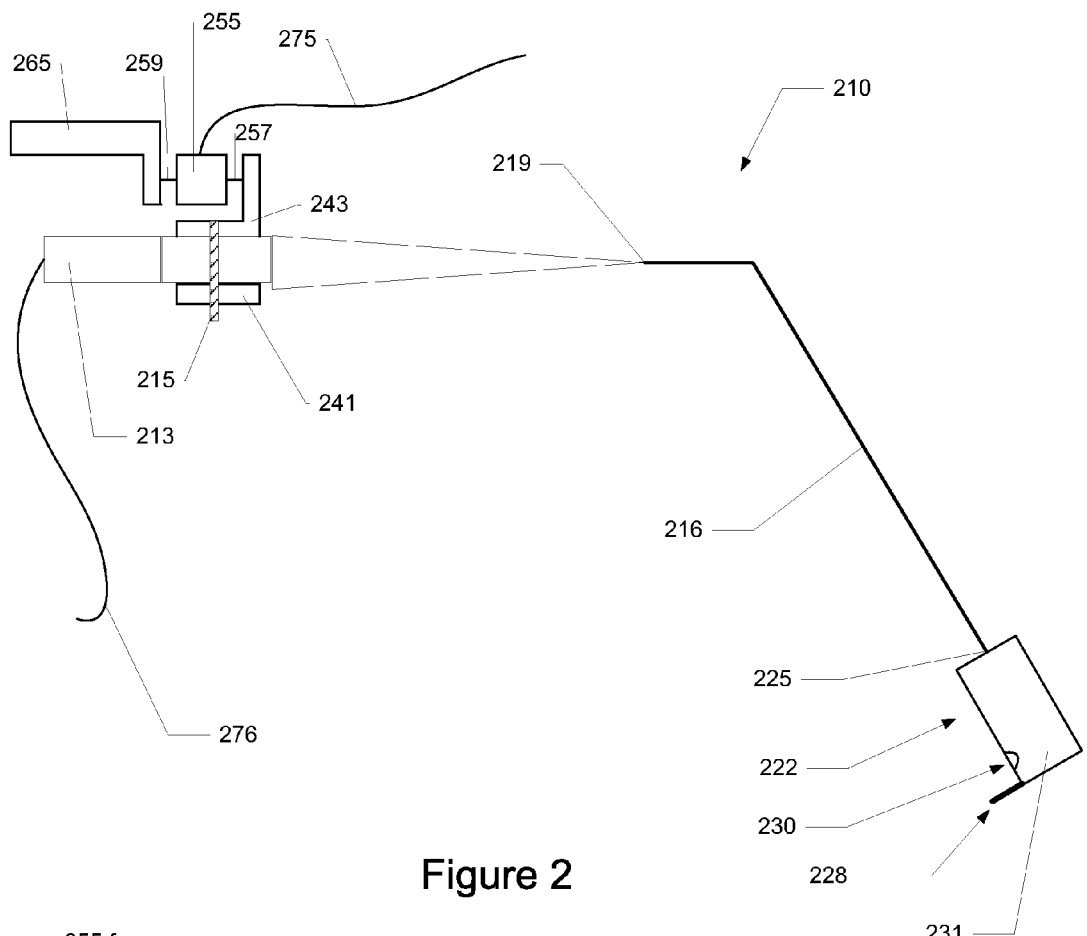
FIG. 2 shows details of an embodiment of a retractor device.

FIG. 2 shows one embodiment of a retractor device. A retractor device 210 includes a retractor that has a first handle 213, a shaft 216 connected at its proximal end 219 to the first handle, and a tip 222 connected to a distal end 225 of the shaft. The shaft can be made of steel. The tip includes a retractor portion or retractor blade 228 and an oximeter sensor 231. Oximeter sensor 231 has one or more sensor openings 230 on a bottom surface of the oximeter sensor, adjacent to retractor blade 228.

The shaft can include an internal channel or passageway. Optical fibers can pass from sensor openings on the tip, through the channel, through the handle, and into a cable jacket or cable insulation. Alternatively, the fibers can be run along the shaft and secured by, for example, shrink wrap. The optical fibers that travel inside or along the shaft are exposed through sensor opening 230 on a bottom surface of tip 222. Cable 276 that includes optical fibers is configured to be connected to a system unit or oximeter console (not shown).

Retractor device 210 also includes a force sensor 255. Force sensor 255 has a first end 257 and a second end 259 on the opposite side of the first end along the axis of force sensor 255. Force sensor 255 measures an amount of force that is applied in a horizontal direction along its axis. First end 257 of force sensor 255 is connected to an L-shaped clamp element 243. L-shaped clamp element 243, together with linear clamp element 241, is clamped to first handle 213 of the retractor by a fastener 215. Second end 259 of force sensor 255 is connected to a second handle 265. Force sensor 255 also has a cable 275 which transmits a signal measured by force sensor 255 to a system unit or force sensor console (not shown).

Retractor device 210 can be used by placing oximeter sensor 231 in contact with a nerve. Light is transmitted from a system unit or console (not shown in FIG. 2), through optical fiber in cable 276, out a sensor opening 230 on tip 222 and into the nerve. The reflected light from the nerve is then received by another sensor opening on the tip, transmitted back to the console via optical fiber, and then processed. The console can display oxygen saturation measurement. The same or separate console can also display an amount of force that is applied by the retractor tip to retract the nerve.

Retractor device 210 has two handles—first handle 213 and second handle 265. When first handle 213 is used to retract a tissue, there is no change in load or force for load cell 255 as it is not being pulled upon. When the tissue is retracted using first handle 213, oxygen saturation measurements of a retracted tissue can be made. However, a force applied to a retracted tissue will not be measured.

When second handle 265 is used to retract a tissue, since the handle is connected to load cell 255, a strain gauge in load cell 255 becomes deformed as the surgeon pulls second handle 265 to retract a tissue. The load or force measured by load cell 255 is converted into an electrical signal which is transmitted to a system unit (not shown) via cable 275. When the tissue is retracted using second handle 265, both oxygen saturation and force measurements can be made.

While FIG. 2 illustrates an embodiment of the invention where the force sensor is attached to a retractor as a separate unit and is pulled upon by a second handle, the force sensor can be an integral part of the retractor itself. For example, the force sensor can be located between first handle 213 and proximal end 219 of the shaft of the retractor. In another example, the force sensor can be located in the middle of shaft 216. In yet another example, the force sensor can be located between distal end 225 of the shaft and retractor tip 222. When the force sensor is integrated as part of a retractor, second handle 265 can be omitted in the device, and first handle 213 can be used to retract or pull aside a tissue.

Figure 3:
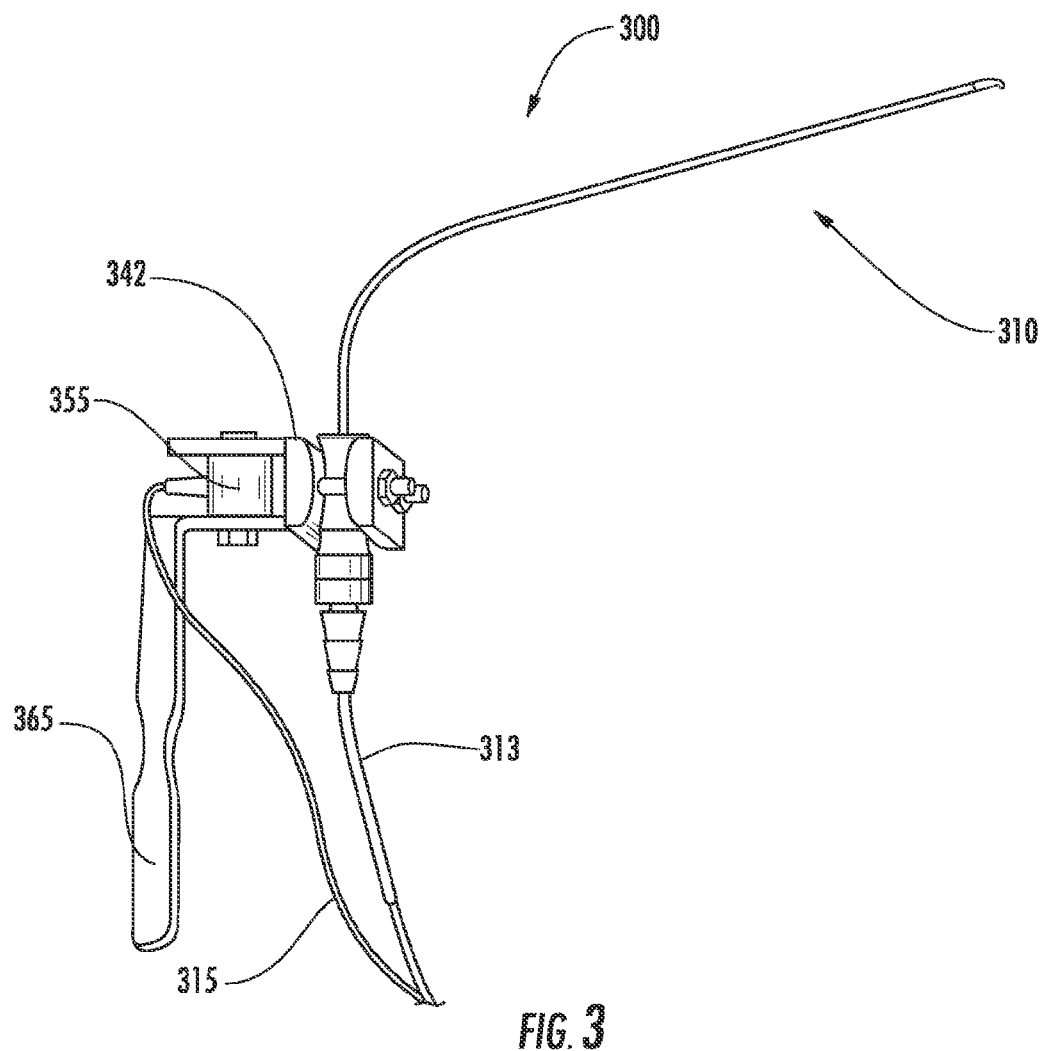
FIG. 3 shows a photograph of mechanical parts of a retractor device.

FIG. 3 shows a photograph of mechanics of a retractor device 300. Retractor device 300 has a retractor 310 that has a tip with an oximeter sensor at a distal end. A handle of retractor 310 is attached to one end of a load cell 355 by a clamp 342. The opposite side of load cell 355 is attached to an aluminum handle 365. The load cell can sense a load ranging between zero to ten pounds. A cable 315 connects load cell 355 to a system unit (not shown). A cable 313 connects the oximeter sensor at the tip of retractor 310 to a system unit (not shown).

Figure 4A:
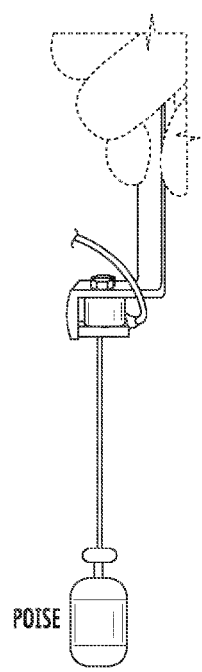
FIG. 4A shows a calibration setup of a load cell, with the axis of the load cell being vertical.
Figure 4B:
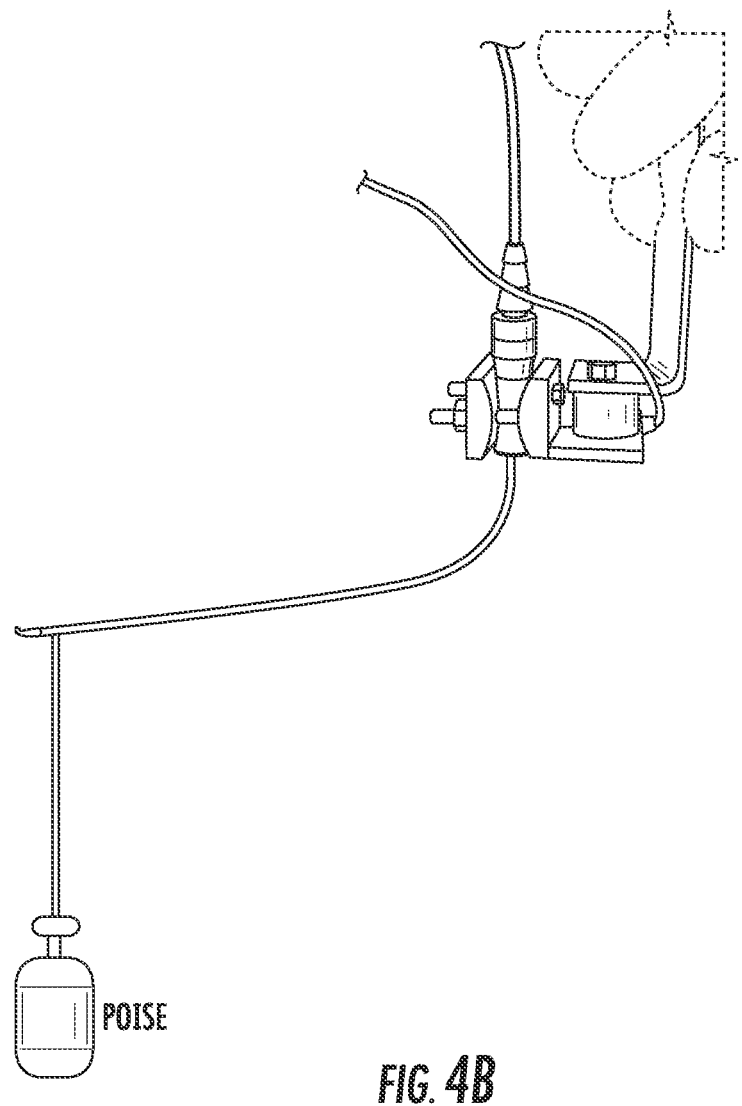
FIG. 4B shows a calibration setup of a retractor device having a load cell, with the axis of the load cell being vertical.
Figure 5:
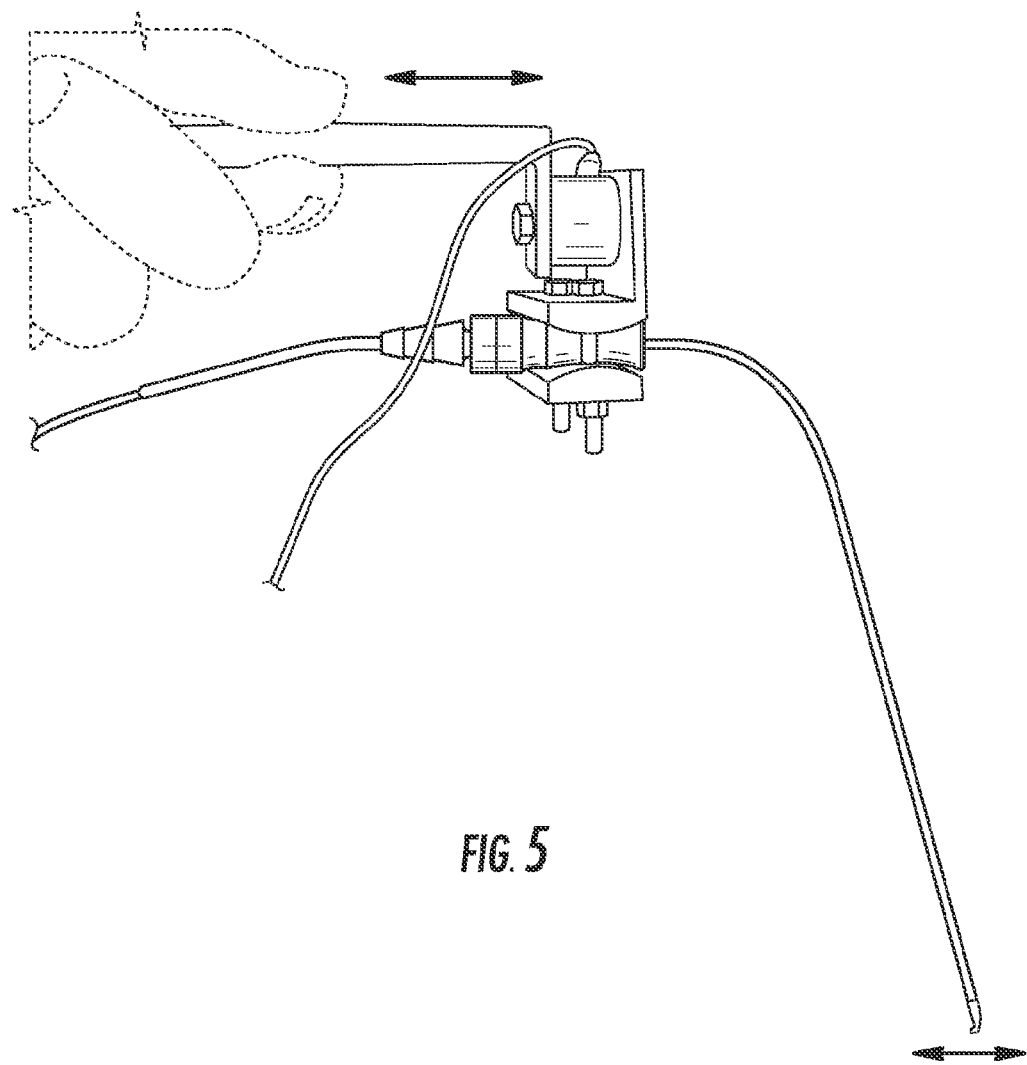
FIG. 5 shows a calibration setup of a retractor device having a load cell, with the axis of the load cell being horizontal.

FIGS. 4A, 4B, and 5 illustrate various setups for calibrating a load cell. Shown in FIGS. 4A, 4B, and 5 is a load cell, such as from Cooper Instruments & Systems, Model LPM 530-HW10 (Warrenton, Va.). The data sheet and users' guide for this load cell is incorporated by reference along with all other references cited in this application. According to the factory calibration, the load cell and amplifier provide one volt of output per one pound of force. The factory calibration is verified by using the setups shown in FIGS. 4A, 4B, and 5.

In FIG. 4A, a poise is attached to one end of the axis of the load cell, and a handle is attached to the other end of the axis of the load cell. As shown in FIG. 4A, the axis of the load cell is vertical. A cable from the load cell is connected to an amplifier, which is then connected to a voltmeter. Therefore, an LCD reading on the voltmeter represents the weight of the poise that is hung vertically on the load cell.

In a first calibration, no poise was attached to the load cell. In a second calibration, a poise weighing 200 grams was attached. In a third calibration, a poise weighing 400 grams was attached. The results are shown in table A.

In the first calibration for the setup shown in FIG. 4A, the voltmeter reading was 0.04 volt. Since no poise was attached in this setup, 0.04 volt represents an offset that is subtracted from the voltmeter reading when weights are attached to the load cell. Accordingly, the calibration equation for the setup shown in FIG. 4A is as follows:

[force used on the load cell]=([LCD reading]−0.04 volt)*4.9 Newton.

This equation agrees with the factory calibration with an error of about 5 percent. It is noted that one kilogram of force equals 2.205 pound of force, which equals 9.8 Newton.

In FIG. 4B, a retractor device shown in FIG. 3 was used to calibrate a poise. As shown in FIG. 4B, the retractor device is held by a second handle attached to a load cell so that the axis of the load cell is vertical. A poise is hung at the tip of the retractor device. Again, voltage measurements were made with zero weight, with a poise weighing 200 grams, and with a poise weighing 400 grams. The results are shown in table A.

When no weight was attached for the setup shown in FIG. 4B, the voltmeter reading was 0.22 volt. Since no poise is attached in this setup, 0.22 volt represents a force due to the weight of the retractor device. Therefore, if the retractor device is to be used as shown in FIG. 4B (i.e., with a force on the retractor device tip being vertical), then the calibration equation is as follows:

[Vertical force used on the retractor tip]=([LCD reading]−0.22 Volt)*4.9 Newton.

FIG. 5 shows how a retractor device is used in retracting a tissue. In this figure, the second handle pulls on a load cell horizontally to the left to retract a tissue. The voltmeter reading without hanging any poise is 0.1 volt as shown in the last column of table A. Therefore, the calibration equation for the setup shown in FIG. 5 is as follows:

[horizontal force on the retractor tip]=([LCD reading]−0.1 volt)*4.9 Newton.

For example, when a retracting force of two Newton is executed onto the retractor device tip along the horizontal direction in FIG. 5, the voltmeter reading should be about 0.51 volt.

TABLE A

| | Calibration Results | | |
|---|---|---|---|
| Weight | LCD reading (Volt) | | |
| (gram) | Figure 4A | Figure 4B | Figure 5 |
| 0 | 0.04 | 0.22 | 0.1 |
| 200 | 0.47 | 0.62 | |
| 400 | 0.97 | 1.04 | |

Figure 6A:
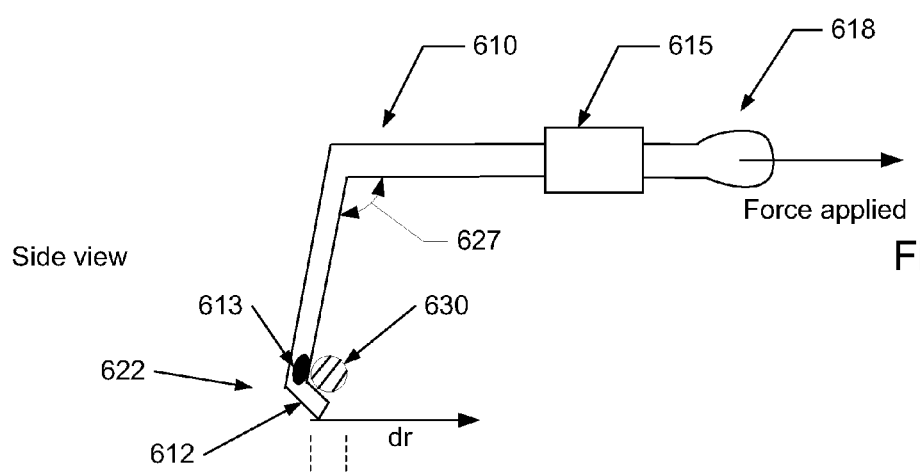
FIG. 6A shows a side view of a retractor device and a direction of force applied.

FIG. 6A illustrates a side view of a retractor device. As shown in FIG. 6A, the retractor device has a force sensor 615 that is connected between an oximeter retractor 610 and a handle 618. Force sensor 615 measures an amount of force applied to a tissue 630 by a retractor tip 622 when handle 618 is pulled to the right to retract the tissue. A retractor portion 612 cradles tissue 630 so that the tissue is ready to be pulled, and oximeter sensor 613 measures an oxygen saturation level of tissue 630 at the point of contact.

Typically, oximeter retractor 610 has a shaft that is angled to assist a surgeon in viewing or retracting a tissue. For example, the shaft may be bent at an angle 627 of about 105 degrees as shown in FIG. 6A. Angle 627 shown in FIG. 6A is merely exemplary, and the shaft may be bent at any suitable angle ranging between 90 and 179 degrees. However, in an embodiment, the shaft can be straight with angle 627 of 180 degrees, and the retractor device is a straight puller.

Figure 6B:
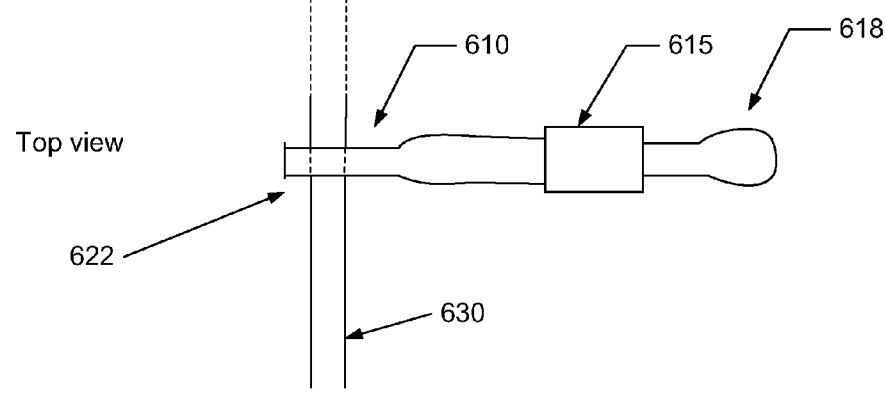
FIG. 6B shows a top view of the retractor device shown in FIG. 6A.

FIG. 6B illustrates a top view of the same retractor device shown in FIG. 6A. As shown, the retractor device includes force sensor 615 which is connected between a tip of oximeter retractor 610 and handle 618, ready to pull nerve 630 resting near tip 622 of the retractor device.

In FIGS. 6A and 6B, when the retractor device is pulled by handle 618 in a horizontal direction to the right, nerve 630 is pulled away from its original, resting position to the right. The distance that nerve 630 travels at the point of contact is referred to as a "retraction distance," shown as $d_r$ in FIG. 6A. When handle 618 pulls the retractor device to the right, then a retraction distance of nerve 630 increases. When the retractor device is returned back to the left, then a retraction distance decreases to a point where the retraction distance equals zero as shown in FIGS. 6A and 6B.

Figure 7:
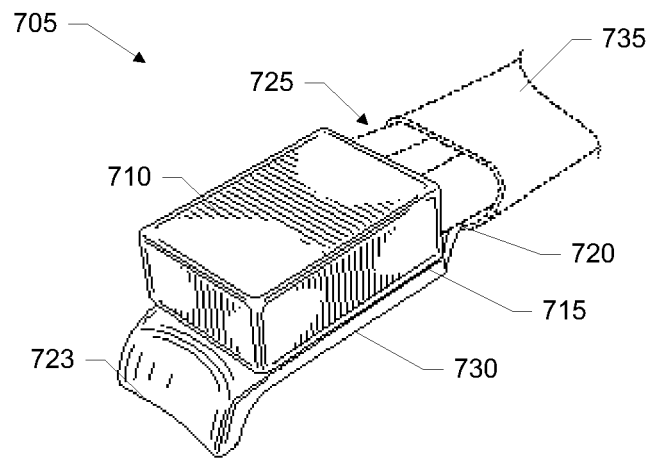
FIG. 7 shows a perspective view of a first implementation of a tip.

FIG. 7 shows a perspective view of a first implementation of a tip 705. The tip includes a retractor blade and an oximeter sensor 710 attached to a top surface 715 of the tip. The tip attaches to a shaft 720. The tip also includes a retractor portion 723. Optical fibers are encased in a cable jacket 725, travel along the shaft, into the oximeter sensor, and are exposed through an opening on a bottom surface 730 of the tip. Cable jacket 725 and shaft are wrapped with a tubing 735. Such tubing may be heat-shrink tubing.

In a specific implementation of FIG. 7, the tip of the retractor has a length of about 17.5 millimeters, width of about 8 millimeters, and a thickness (not including the retractor blade) of about 5 millimeters.

Figure 8:
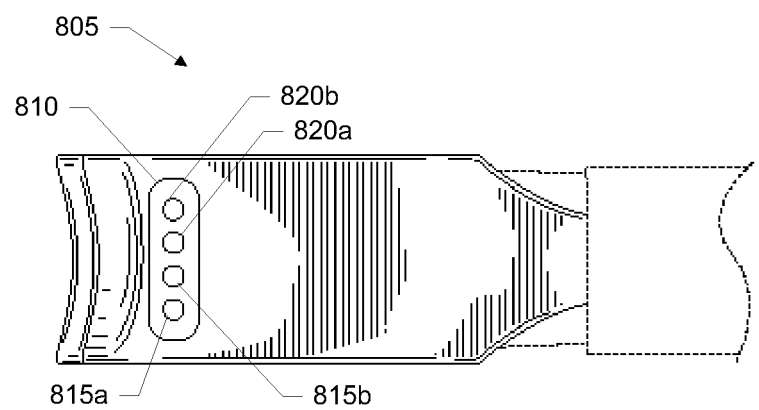
FIG. 8 shows a bottom view of the first implementation of a tip.

FIG. 8 shows a bottom view of the first implementation of a tip 805. The tip has a retractor blade and slot 810, within which there are sensor openings. There are four sensor openings for ends of fiber optic cables. The openings 815*a*, 815*b*, 820*a*, and 820*b* are for source and detector fibers.

Figure 9:
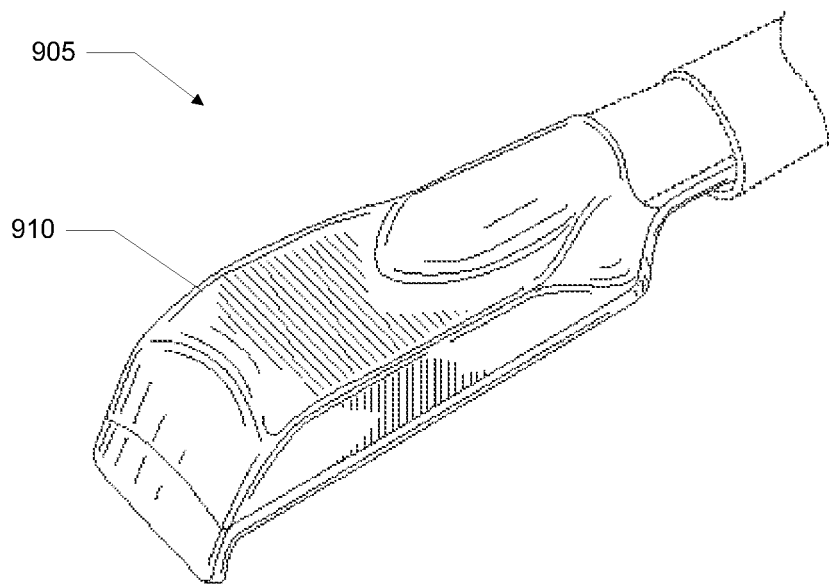
FIG. 9 shows a perspective view of a second implementation of a tip.

FIG. 9 shows a perspective view of a second implementation of a tip 905 with an encasement 910 which contains optical fiber attached to the tip.

In a specific implementation of FIG. 9, the tip of the retractor has a length of about 17.5 millimeters, width of about 8 millimeters, and a thickness (not including the retractor blade) of about 3 millimeters.

Figure 10:
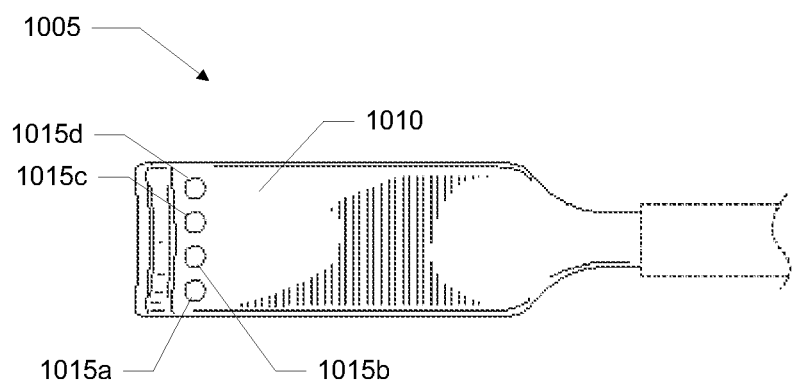
FIG. 10 shows a bottom view of the second implementation of a tip.

FIG. 10 shows a bottom view of the second implementation of a tip 1005. The tip includes a retractor blade and four sensor openings on a bottom surface 1010 of the tip. The sensor openings include openings 1015*a*, 1015*b*, 1015*c*, and 1015*d*. Optical fiber is connected to each of the sensor openings. The sensor openings can include sources and detectors.

Figure 11:
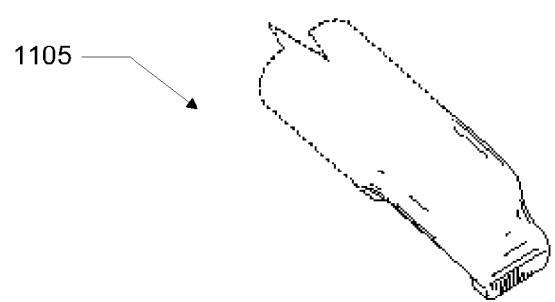
FIG. 11 shows a perspective view of a third implementation of a tip.

FIG. 11 shows a perspective view of a third implementation of a tip 1105.

Figure 12:
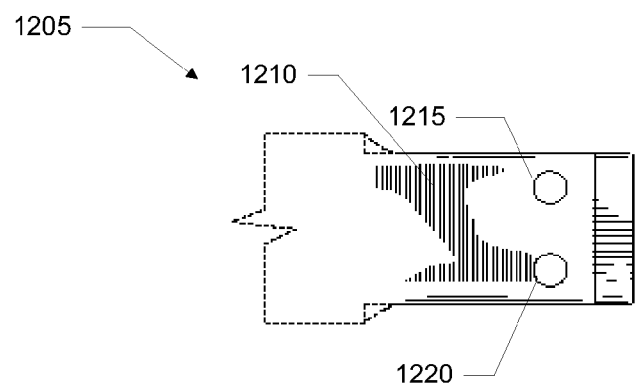
FIG. 12 shows a bottom view of the third implementation of a tip.

FIG. 12 shows a bottom view of the third implementation of a tip 1205. The tip includes two sensor openings on a bottom surface 1210 of the tip. The two sensor openings include an opening 1215 and an opening 1220. The openings include a source and detector.

Figure 13:
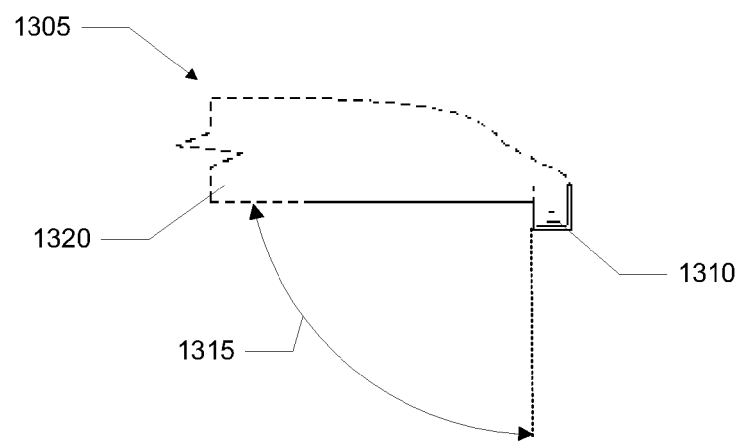
FIG. 13 shows a side view of the third implementation of a tip.

FIG. 13 shows a side view of the third implementation of a tip 1305. A retractor portion or retractor blade 1310 is at an angle 1315 to a shaft 1320 onto which the tip is attached. In an implementation, the angle is about 90 degrees. Angle 1315 ranges from about 90 degrees to about 179 degrees.

In a specific implementation of FIG. 13, the tip of the retractor has a length of about 5 millimeters, width of about 3 millimeters, and a thickness (not including the retractor blade) of about 2 millimeters.

Figure 14:
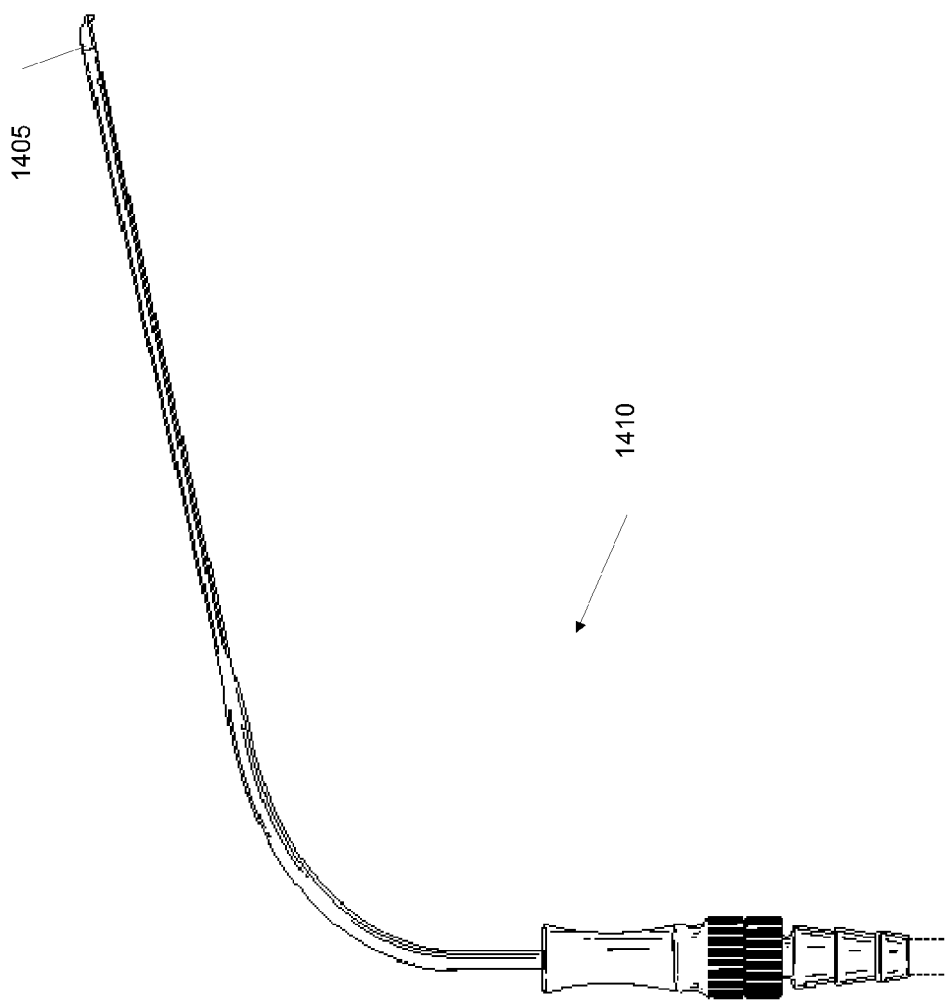
FIG. 14 shows a perspective view of the third implementation of the tip attached to a nerve retractor.

FIG. 14 shows a side view of the third implementation of the tip 1405 connected to a nerve retractor 1410. This figure shows the handle of the retractor, which connects to the shaft and the tip.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A device comprising:
a retractor, for retracting a tissue, comprising a shaft, a first member coupled to a proximal end of the shaft, and a tip coupled to a distal end of the shaft, wherein the tip comprises a retractor portion and an oximeter sensor;
a force sensor operatively coupled to the retractor via the first member; and
a second member, wherein the force sensor comprises a first connection point and a second connection point, and the first connection point of the force sensor is coupled to the first member and the second member is coupled to the second connection point of the force sensor.

2. The device of claim 1 wherein the first connection point and the second connection point are on opposite sides of each other.

3. The device of claim 2 wherein the oximeter sensor comprises a first sensor opening and a second sensor opening on a bottom side of the tip.

4. The device of claim 1 wherein the force sensor comprises a cable which is configured to transmit a signal representing an amount of force measured by the force sensor.

5. The device of claim 1 wherein the force sensor is a load cell.

6. The device of claim 1 wherein the force sensor is located between the first member and the tip of the retractor.

7. The device of claim 1 wherein the oximeter sensor comprises a first sensor opening and a second sensor opening on a bottom side of the tip.

8. The device of claim 7 further comprising:
a first optical fiber; and
a second optical fiber, wherein the first optical fiber passes through a channel in the shaft and a distal end of the first optical fiber is coupled to the first sensor opening of the tip, and
the second optical fiber passes through the channel in the shaft and a distal end of the second optical fiber is coupled to the second sensor opening of the tip.

9. The device of claim 1 wherein the force sensor comprises a cable which is configured to transmit a signal representing an amount of force measured by the force sensor,
the force sensor is a load cell,
the force sensor is located between the first member and the tip of the retractor,
the force sensor has a first end and a second end, wherein the first end and the second end are on opposite sides of each other, and wherein the first end of the force sensor is coupled to the first member and the second member is coupled to the second end of the force sensor,
the oximeter sensor comprises a first sensor opening and a second sensor opening on a bottom side of the tip, and
the device comprises:
a first optical fiber;
a second optical fiber, wherein the first optical fiber passes through a channel in the shaft and a distal end of the first optical fiber is coupled to the first sensor opening of the tip, and
the second optical fiber passes through the channel in the shaft and a distal end of the second optical fiber is coupled to the second sensor opening of the tip.

10. A device comprising:
a retractor, for retracting a tissue, comprising a shaft, a first member coupled to a proximal end of the shaft, and a tip coupled to a distal end of the shaft, wherein the tip comprises a retractor portion and an oximeter sensor;
a force sensor operatively coupled to the retractor; and
a second member, wherein the force sensor has a first end and a second end, the first end and the second end are on opposite sides of each other, and the first end of the force sensor is coupled to the first member and the second member is coupled to the second end of the force sensor.

11. The device of claim 10 wherein the force sensor comprises a cable which is configured to transmit a signal representing an amount of force measured by the force sensor.

12. The device of claim 10 wherein the force sensor is a load cell.

13. The device of claim 10 wherein the force sensor is located between the first member and the tip of the retractor.

14. The device of claim 10 wherein the oximeter sensor comprises a first sensor opening and a second sensor opening on a bottom side of the tip.

15. The device of claim 14 further comprising:

a first optical fiber; and a second optical fiber, wherein the first optical fiber passes through a channel in the shaft and a distal end of the first optical fiber is coupled to the first sensor opening of the tip, and the second optical fiber passes through the channel in the shaft and a distal end of the second optical fiber is coupled to the second sensor opening of the tip.

16. The device of claim 10 wherein the force sensor comprises a cable which is configured to transmit a signal representing an amount of force measured by the force sensor, the force sensor is a load cell, the force sensor is located between the first member and the tip of the retractor, the force sensor has a first end and a second end, wherein the first end and the second end are on opposite sides of each other, and wherein the first end of the force sensor is coupled to the first member and the second member is coupled to the second end of the force sensor, the oximeter sensor comprises a first sensor opening and a second sensor opening on a bottom side of the tip, and the device comprises:

a first optical fiber;

a second optical fiber, wherein the first optical fiber passes through a channel in the shaft and a distal end of the first optical fiber is coupled to the first sensor opening of the tip, and the second optical fiber passes through the channel in the shaft and a distal end of the second optical fiber is coupled to the second sensor opening of the tip.

17. A method comprising:

providing a retractor with a first member, a shaft, and a tip having a bottom portion and a blade portion;

forming at least two openings in the bottom portion of the retractor;

attaching a force sensor to the first member; and attaching a second member to the force sensor.

18. The method of claim 17 comprising:

connecting a first fiber optic cable to a first opening of the at least two openings; and connecting a second fiber optic cable to a second opening of the at least two openings.

19. The method of claim 17 comprising:

removing at least a portion of the first member which is not attached to the force sensor.

20. The method of claim 17 wherein a first angle between the second member and the shaft is from about 80 degrees to 120 degrees.

21. The method of claim 20 wherein a second angle between the blade portion and the bottom portion is from about 90 degrees to about 115 degrees.

* * * * *